Figure 1:
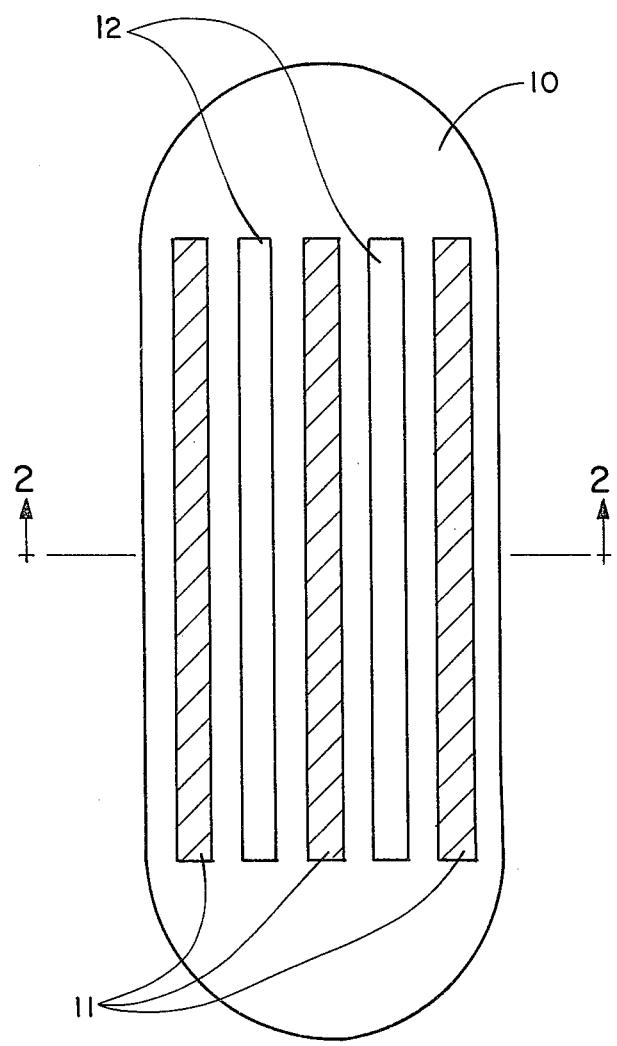

United States Patent [19]

Roeder

[11] 4,337,772

[45] Jul. 6, 1982

[54] ADHESIVE BACKED SANITARY NAPKIN

[75] Inventor: Robert J. Roeder, Appleton, Wis.

[73] Assignee: Kimberly-Clark Corporation, Neenah, Wis.

[21] Appl. No.: 241,252

[22] Filed: Mar. 6, 1981

[51] Int. Cl.³ .............................................. A61F 13/16
[52] U.S. Cl. ......................... 128/290 R; 128/DIG. 30
[58] Field of Search ............ 128/284, 286, 287, 290 R

[56] References Cited

U.S. PATENT DOCUMENTS

| | | | |
|---|---|---|---|
| 3,672,371 | 6/1972 | Roeder | 128/DIG. 30 |
| 3,967,624 | 7/1976 | Milnamon | 128/DIG. 30 |
| 4,023,570 | 5/1977 | Chinai et al. | 128/290 R |
| 4,063,559 | 12/1977 | Tritsch | 128/287 |
| 4,067,337 | 1/1978 | Ness | 128/DIG. 30 |
| 4,195,634 | 1/1980 | DiSalvo et al. | 128/DIG. 30 |

Primary Examiner—C. Fred Rosenbaum
Attorney, Agent, or Firm—Howard Olevsky; William D. Herrick

[57] ABSTRACT

A sanitary napkin is provided in which the pressure sensitive adhesive means utilized for attachment of the napkin are separated from each other by a pattern of nonpressure sensitive adhesive which may be similar to the pattern of the pressure sensitive adhesive positioned on the garment facing side of a sanitary napkin but is from two to ten times greater in thickness.

5 Claims, 5 Drawing Figures

ADHESIVE BACKED SANITARY NAPKIN

FIELD OF THE INVENTION

The subject invention relates to a sanitary napkin and particularly to a sanitary napkin having a garment suspension adhesive attached thereto.

BACKGROUND OF THE INVENTION

The so-called tabless napkins have become increasingly popular over the past several years. These napkins rather than having extended areas at either end for attachment by means of a belt have an adhesive pattern on the garment facing side thereof for direct attachment to the garment. Napkins may have this adhesive applied directly to a fluid impervious baffle or to a fluid permeable outer wrap which is overwrapped in the adhesive area. In any event, however, adhesives utilized for attachment to undergarments have been of the pressure sensitive variety and are traditionally covered with a release liner. This release liner is usually a silicone treated release paper and is maintained with low adhesive force on the pressure sensitive adhesive until the napkin is ready for use. The release liner is peeled away and the napkin is then pressed into place activating the pressure sensitive adhesive by the force utilized in producing the contact with the undergarment.

There have been problems associated with the utilization of release liners, however. For example, a separate manufacturing step is necessary to attach the release liners. Furthermore, the properties of the adhesive must be matched to that of the release surface to provide sufficient adhesion for release liner attachment without providing a strong adhesive bond requiring substantial force to separate the release liner. Improper coating of the release liner can bring about a direct paper to adhesive bond which produces nonadhesive areas on the adhesive strip when release is attempted and, in extreme cases, can render the napkin unusable due to the defect in the attachment system.

In the past, there have been attempts to eliminate the release liner from sanitary napkins. These attempts have, however, met with indifferent success. German Pat. No. 2,644,032 teaches a self-adhesive napkin in which the adhesive is insulated from contact by a perforated polyurethane foam.

U.S. Pat. No. 4,067,337 discloses a diaper tape which needs no protective release sheet because of the utilization of an open plastic netting which prevents direct contact with the pressure sensitive adhesive. While the problems inherent in this attachment means are substantially different than those utilized with a sanitary napkin, the broad approach to the solution is somewhat similar to that taught in the German Patent referred to above. U.S. Pat. Nos. 4,010,753 and 3,853,129 show structures similar to those disclosed in U.S. Pat. No. 4,067,337.

It is apparent that both the feminine napkin art and the art associated with diapers relies upon the the introduction of a covering layer in which the adhesive is made available by expressing the adhesive surface through the covering. The subject invention provides an alternative approach for eliminating release liners while providing a sanitary napkin which can be rapidly made on essentially conventional equipment.

SUMMARY OF THE INVENTION

This invention provides a sanitary napkin in which the adhesive attachment means located on the garment facing side of the adhesive are shielded by corresponding patterns of nonpressure sensitive adhesive having a thickness of from about two to ten times that of the pressure sensitive adhesive layer. (The pressure sensitive adhesive layer is between 2 and 6 mils thick.) These nonpressure sensitive adhesives which are traditionally so-called hot melt adhesives are adhesive when they are applied in the hot state but lose their adhesive properties when they are at room temperature. These nonpressure sensitive adhesives are therefore applied hot to a specific thickness and then allowed to cool. In so doing, they provide a substantially nontacky barrier. The pressure sensitive adhesive which can be applied simultaneously, subsequently or prior to the application of the hot melt adhesives is not directly exposed to a surface which might otherwise adhere to it until the sanitary napkin is to be used. The curvature of the sanitary napkin as it is placed in position against an undergarment exposes the pressure sensitive adhesive for the first time to the undergarment and maintains the desired attachment. The nonpressure sensitive hot melt adhesive provides no barrier to attachment due to the configuration of the napkin resulting from its positioning.

It is currently preferred that the pressure sensitive adhesive be applied in a separate step and the particular pattern may determine the method of application. The number of separate elements of the pattern favor utilization of adhesive printing equipment. The hot melt adhesive which may be polyvinyl pyrollidone for example, is currently preferred to be applied in a separate extrusion step. In any event, both adhesives can be applied by conventionally available equipment and if the pressure sensitive adhesive is also a hot melt adhesive such as that disclosed, for example, in U.S. Pat. No. 4,136,699 issued to the H. B. Fuller Company, the adhesive can all be applied simultaneously by extrusion.

Figure 2:
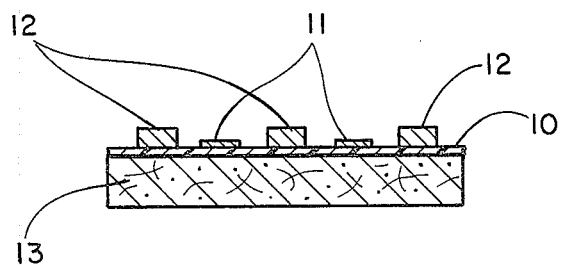

The concept of the invention will be more readily understood by reference to the drawings in which FIGS. 1, 3, 4 and 5 show plan views of alternative embodiments of the napkin of this invention and FIG. 2 is a bottom cross sectional view of the napkin according to this invention.

As can be seen in FIG. 1 the garment facing side 10 of the sanitary napkin is provided with alternating strips of adhesive. The outermost longitudinal strips 11 are the nonpressure sensitive shielding adhesive strips while the alternating strips 12 are the pressure sensitive adhesive strips which will attach the napkin to the undergarment during use. As can be seen in FIG. 2, a sanitary napkin having an absorbent component 13 and a baffle 10 has nonpressure sensitive adhesive strips 11 of substantially greater thickness than pressure sensitive adhesive strips 12.

Figure 3:
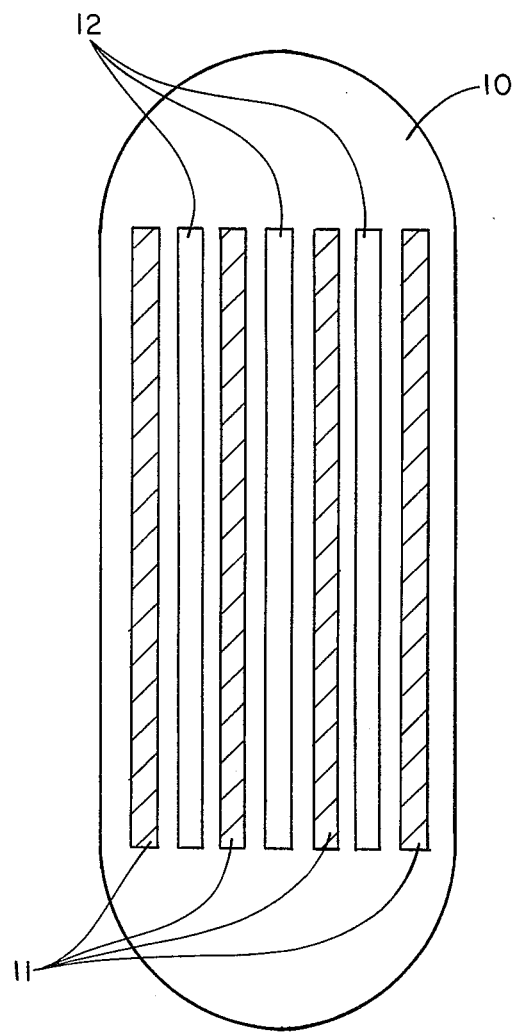

The sanitary napkin depicted in FIG. 3 is a currently preferred configuration in which three pressure sensitive adhesive strips are separated by nonpressure sensitive adhesive strips in alternate rows. As can be seen from both FIGS. 1 and 3, the outermost strip is not pressure sensitive adhesive and serves to guide the edge of the napkin from premature adhesive contact as well as provide a barrier for unwanted adhesive contact at the side edge of the napkin during use.

Figure 4:
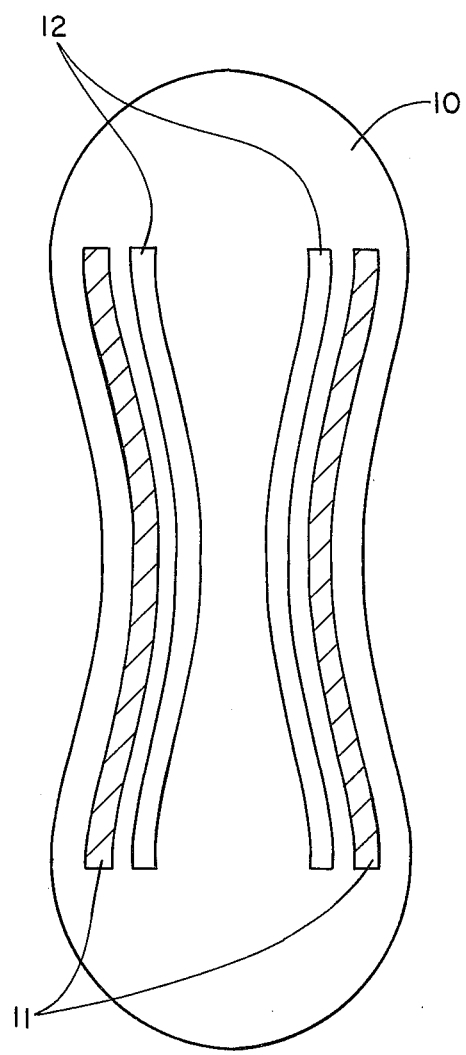

FIG. 4 is another embodiment in which the longitudinal edges of the sanitary napkin have been cut in a modified hourglass shape to more conform with the configuration of the body in the area of the crotch. In this instance it is generally preferble to match the configuration of all of the adhesive strips with the configuration of the longitudinal edge of the napkin.

Figure 5:
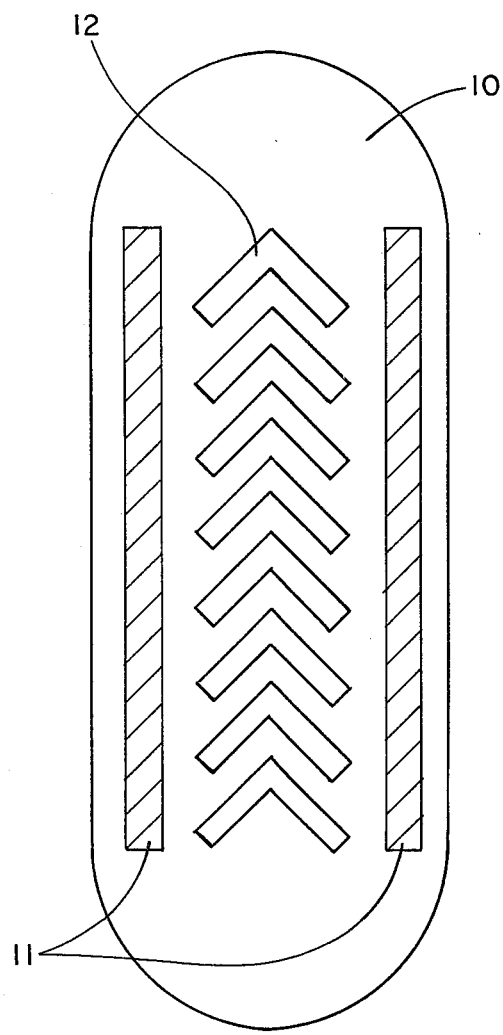

FIG. 5 shows an alternative embodiment in which there is not a precise geometrical correlation between the pressure sensitive adhesive configuration 12 and the nonpressure sensitive shielding configuration 11. In this instance, the pressure sensitive adhesive is in a chevron configuration located near the center of the pad but premature exposure is prevented by the utilization of longitudinally oriented nonpressure sensitive adhesive strips near the outer longitudinal edges of the pad.

It will be readily apparent to those skilled in the art that a variety of adhesive patterns can be utilized both for the pressure sensitive and the nonpressure sensitive adhesive component. It is possible to utilize a random pattern rather than the chevron pattern set forth in FIG. 5 for example. An alternative which is readily apparent is perpendicular strips of pressure sensitive adhesive utilized in the same general configuration as shown in FIG. 5. It is also well known in the art to utilize adhesive beads rather than continuous strips. This is contemplated within the scope of the subject invention. As long as the nonpressure sensitive adhesive component is located between the pressure sensitive adhesive and the outer longitudinal edges of the napkin the goal of the subject invention will be accomplished. At some point it may even be desirable to utilize nonpressure sensitive adhesive at the ends of the napkin and such use is indeed contemplated within the scope of this invention.

What is claimed is:

1. A sanitary napkin with a body facing surface and a garment facing surface comprising in combination an absorbent batt, a fluid impermeable baffle positioned between the batt and the garment of the wearer and adhesive attachment means on the garment facing side said attachment means including a plurality of discrete portions of pressure sensitive adhesive terminating before the ends of the garment facing surface at least partially separated by discrete portions of nonpressure sensitive adhesive having a thickness two to ten times that of the pressure sensitive adhesive.

2. The napkin according to claim 1 wherein the pressure sensitive adhesive pattern corresponds to the configuration of the longitudinal sides of the napkin.

3. The napkin according to claim 1 wherein the pressure sensitive adhesive portion is present in longitudinal strips separated by longitudinal strips of nonpressure sensitive adhesive.

4. The napkin according to claim 1 wherein the pressure sensitive adhesive pattern comprises three longitudinal strips.

5. The sanitary napkin of claims 1, 2, 3 or 4 wherein the pressure sensitive adhesive is spaced inward from the longitudinal edges of the pad and a portion of the nonpressure sensitive adhesive pattern is positioned between the longitudinal edges and the outermost portion of the pressure sensitive adhesive pattern.

* * * * *